(12) United States Patent
Albert et al.

(10) Patent No.: US 11,382,554 B2
(45) Date of Patent: *Jul. 12, 2022

(54) HEART MONITORING SYSTEM USABLE WITH A SMARTPHONE OR COMPUTER

(71) Applicant: AliveCor, Inc., Mountain View, CA (US)

(72) Inventors: David Albert, Oklahoma City, OK (US); Bruce Richard Satchwell, Carrara (AU); Kim Norman Barnett, Mt. Tamborine (AU)

(73) Assignee: AliveCor, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/486,777

(22) Filed: Apr. 13, 2017

(65) Prior Publication Data

US 2017/0215755 A1 Aug. 3, 2017

Related U.S. Application Data

(60) Continuation of application No. 13/964,490, filed on Aug. 12, 2013, now Pat. No. 9,649,042, which is a
(Continued)

(51) Int. Cl.
*A61B 5/332* (2021.01)
*A61B 5/00* (2006.01)
(Continued)

(52) U.S. Cl.
CPC ............ *A61B 5/332* (2021.01); *A61B 5/0205* (2013.01); *A61B 5/02416* (2013.01);
(Continued)

(58) Field of Classification Search
None
See application file for complete search history.

(56) References Cited

U.S. PATENT DOCUMENTS 3,717,857 A 2/1973 Evans
3,731,311 A 5/1973 Williams
(Continued)

FOREIGN PATENT DOCUMENTS

CH 675675 A5 10/1990
CN 1798522 A 7/2006
(Continued)

OTHER PUBLICATIONS

Adidas miCoach Pacer Review: Like Nike+, Only Better; printed from website http://gizmodo.com/5479456/adidas* printed on Mar. 4, 2010* 5 pages.
(Continued)

*Primary Examiner* — Michael W Kahelin
*Assistant Examiner* — Elizabeth K So
(74) *Attorney, Agent, or Firm* — Womble Bond Dickinson (US) LLP (57) ABSTRACT

A personal monitoring device has a sensor assembly configured to sense physiological signals upon contact with a user's skin. The sensor assembly produces electrical signals representing the sensed physiological signals. A converter assembly, integrated with, and electrically connected to the sensor assembly, converts the electrical signals generated by the sensor assembly to a frequency modulated physiological audio signal having a carrier frequency in the range of from about 6 kHz to about 20 kHz.

10 Claims, 4 Drawing Sheets

Related U.S. Application Data division of application No. 12/796,188, filed on Jun. 8, 2010, now Pat. No. 8,509,882.

(51) Int. Cl.
    *A61B 5/282*     (2021.01)
    *A61B 5/318*     (2021.01)
    *A61B 5/369*     (2021.01)
    *A61B 5/389*     (2021.01)
    *A61B 5/0205*     (2006.01)
    *A61B 5/024*     (2006.01)
    *A61B 5/055*     (2006.01)
    *A61B 5/08*     (2006.01)

(52) U.S. Cl.
    CPC .......... *A61B 5/02438* (2013.01); *A61B 5/282* (2021.01); *A61B 5/318* (2021.01); *A61B 5/369* (2021.01); *A61B 5/389* (2021.01); *A61B 5/6898* (2013.01); *A61B 5/742* (2013.01); *A61B 5/055* (2013.01); *A61B 5/0816* (2013.01); *A61B 2505/07* (2013.01); *A61B 2560/045* (2013.01); *A61B 2560/0468* (2013.01)

(56) References Cited

U.S. PATENT DOCUMENTS

| | | | |
|---|---|---|---|
| 3,768,014 | A | 10/1973 | Smith et al. |
| 3,776,228 | A | 12/1973 | Semler |
| 3,779,237 | A | 12/1973 | Goeltz et al. |
| 3,779,249 | A | 12/1973 | Semler |
| 3,782,367 | A | 1/1974 | Hochberg et al. |
| 3,805,227 | A | 4/1974 | Lester |
| 3,882,277 | A | 5/1975 | Depedro et al. |
| 3,885,552 | A | 5/1975 | Kennedy |
| 3,898,984 | A | 8/1975 | Mandel et al. |
| 3,909,599 | A | 9/1975 | Trott, Jr. et al. |
| 4,027,146 | A | 5/1977 | Gilmore |
| 4,045,767 | A | 8/1977 | Nishihara et al. |
| 4,083,366 | A | 4/1978 | Gombrich et al. |
| 4,095,050 | A | 6/1978 | Beachem et al. |
| 4,221,223 | A | 9/1980 | Linden |
| 4,230,127 | A | 10/1980 | Larson |
| 4,231,031 | A | 10/1980 | Crowther et al. |
| 4,250,888 | A | 2/1981 | Grosskopf |
| 4,281,664 | A | 8/1981 | Duggan |
| 4,295,472 | A | 10/1981 | Adams |
| 4,312,358 | A | 1/1982 | Barney |
| 4,318,130 | A | 3/1982 | Heuer |
| 4,364,397 | A | 12/1982 | Citron et al. |
| 4,367,752 | A | 1/1983 | Jimenez et al. |
| 4,409,984 | A | 10/1983 | Dick |
| 4,531,527 | A | 7/1985 | Reinhold, Jr. et al. |
| 4,567,883 | A | 2/1986 | Langer et al. |
| 4,572,182 | A | 2/1986 | Royse |
| 4,580,250 | A | 4/1986 | Kago et al. |
| 4,583,553 | A | 4/1986 | Shah et al. |
| 4,622,979 | A | 11/1986 | Katchis et al. |
| 4,625,730 | A | 12/1986 | Fountain et al. |
| 4,803,625 | A | 2/1989 | Fu et al. |
| 4,889,131 | A | 12/1989 | Salem et al. |
| 4,920,489 | A | 4/1990 | Hubelbank et al. |
| 4,938,228 | A | 7/1990 | Righter et al. |
| 4,938,229 | A | 7/1990 | Bergelson et al. |
| 4,958,641 | A | 9/1990 | Digby et al. |
| 4,977,899 | A | 12/1990 | Digby et al. |
| 4,981,141 | A | 1/1991 | Segalowitz |
| 5,012,814 | A | 5/1991 | Mills et al. |
| 5,023,906 | A | 6/1991 | Novas |
| 5,025,794 | A | 6/1991 | Albert et al. |
| 5,058,597 | A | 10/1991 | Onoda et al. |
| 5,090,418 | A | 2/1992 | Squires et al. |
| 5,111,396 | A | 5/1992 | Mills et al. |
| 5,128,552 | A | 7/1992 | Fang et al. |
| 5,136,555 | A | 8/1992 | Gardos |
| 5,181,552 | A | 1/1993 | Eiermann |
| 5,191,891 | A | 3/1993 | Righter |
| 5,201,321 | A | 4/1993 | Fulton |
| 5,218,969 | A | 6/1993 | Bredesen et al. |
| 5,226,424 | A | 7/1993 | Bible |
| 5,238,001 | A | 8/1993 | Gallant et al. |
| D341,659 | S | 11/1993 | Homayoun et al. |
| 5,259,387 | A | 11/1993 | Depinto |
| 5,301,679 | A | 4/1994 | Taylor |
| 5,304,186 | A | 4/1994 | Semler et al. |
| 5,313,953 | A | 5/1994 | Yomtov et al. |
| 5,321,618 | A | 6/1994 | Gessman |
| 5,333,616 | A | 8/1994 | Mills et al. |
| 5,336,245 | A | 8/1994 | Adams et al. |
| 5,337,752 | A | 8/1994 | Reeves |
| 5,339,824 | A | 8/1994 | Engira |
| 5,343,869 | A | 9/1994 | Pross et al. |
| 5,343,870 | A | 9/1994 | Gallant et al. |
| 5,348,008 | A | 9/1994 | Bornn et al. |
| 5,360,005 | A * | 11/1994 | Wilk .................. A61B 8/00 600/437 |
| 5,365,935 | A | 11/1994 | Righter et al. |
| 5,410,587 | A | 4/1995 | Grunwell |
| 5,417,222 | A | 5/1995 | Dempsey et al. |
| 5,433,736 | A | 7/1995 | Nilsson |
| 5,452,356 | A | 9/1995 | Albert |
| 5,466,246 | A | 11/1995 | Silvian |
| 5,467,773 | A | 11/1995 | Bergelson et al. |
| 5,481,255 | A | 1/1996 | Albert et al. |
| 5,503,158 | A | 4/1996 | Coppock et al. |
| 5,518,001 | A | 5/1996 | Snell |
| 5,522,396 | A | 6/1996 | Langer et al. |
| 5,539,705 | A | 7/1996 | Akerman et al. |
| D372,785 | S | 8/1996 | Sabri et al. |
| 5,544,661 | A | 8/1996 | Davis et al. |
| 5,551,953 | A | 9/1996 | Lattin et al. |
| 5,561,712 | A | 10/1996 | Nishihara |
| 5,568,448 | A | 10/1996 | Tanigushi et al. |
| 5,579,284 | A | 11/1996 | May |
| D377,983 | S | 2/1997 | Sabri et al. |
| 5,608,723 | A | 3/1997 | Felsenstein |
| 5,634,468 | A | 6/1997 | Platt et al. |
| 5,652,570 | A | 7/1997 | Lepkofker |
| 5,661,699 | A | 8/1997 | Sutton |
| 5,675,325 | A | 10/1997 | Taniguchi et al. |
| 5,678,562 | A | 10/1997 | Sellers |
| 5,701,894 | A | 12/1997 | Cherry et al. |
| 5,704,364 | A | 1/1998 | Saltzstein et al. |
| 5,724,025 | A | 3/1998 | Tavori |
| 5,730,143 | A | 3/1998 | Schwarzberg |
| 5,735,285 | A | 4/1998 | Albert et al. |
| 5,742,251 | A | 4/1998 | Gerber |
| 5,748,103 | A | 5/1998 | Flach et al. |
| 5,764,763 | A | 6/1998 | Jensen et al. |
| 5,772,586 | A | 6/1998 | Heinonen et al. |
| 5,818,788 | A | 10/1998 | Kimura et al. |
| 5,825,718 | A | 10/1998 | Ueki et al. |
| 5,827,179 | A | 10/1998 | Lichter et al. |
| 5,840,020 | A | 11/1998 | Heinonen et al. |
| 5,844,997 | A | 12/1998 | Murphy, Jr. |
| 5,861,018 | A | 1/1999 | Feierbach |
| 5,873,369 | A | 2/1999 | Laniado et al. |
| 5,876,351 | A | 3/1999 | Rohde |
| 5,877,675 | A | 3/1999 | Rebstock et al. |
| 5,889,730 | A | 3/1999 | May |
| 5,929,761 | A | 7/1999 | Van Der Laan et al. |
| D414,870 | S | 10/1999 | Saltzstein et al. |
| 5,970,388 | A | 10/1999 | Will |
| 5,976,083 | A | 11/1999 | Richardson et al. |
| 5,982,297 | A | 11/1999 | Welle |
| 5,983,127 | A | 11/1999 | Depinto |
| 6,008,703 | A | 12/1999 | Perrott et al. |
| 6,024,705 | A | 2/2000 | Schlager et al. |
| 6,037,704 | A | 3/2000 | Welle |
| 6,047,206 | A | 4/2000 | Albrecht et al. |
| 6,047,257 | A | 4/2000 | Dewaele |
| 6,048,319 | A | 4/2000 | Hudgins et al. |
| D427,315 | S | 6/2000 | Saltzstein et al. |

(56) References Cited

U.S. PATENT DOCUMENTS

| | | |
|---|---|---|
| 6,072,396 A | 6/2000 | Gaukel |
| 6,083,248 A | 7/2000 | Thompson |
| 6,084,510 A | 7/2000 | Lemelson et al. |
| 6,102,856 A | 8/2000 | Groff et al. |
| 6,153,532 A | 11/2000 | Dow et al. |
| 6,159,147 A | 12/2000 | Lichter et al. |
| 6,198,394 B1 | 3/2001 | Jacobsen et al. |
| 6,224,548 B1 | 5/2001 | Gopinathan et al. |
| 6,236,889 B1 | 5/2001 | Soykan et al. |
| 6,264,614 B1 | 7/2001 | Albert et al. |
| 6,282,440 B1 | 8/2001 | Brodnick et al. |
| 6,282,441 B1 | 8/2001 | Raymond et al. |
| 6,289,238 B1 | 9/2001 | Besson et al. |
| 6,319,201 B1 | 11/2001 | Wilk |
| 6,343,049 B1 | 1/2002 | Toda |
| 6,363,139 B1 | 3/2002 | Zurek et al. |
| 6,364,834 B1 | 4/2002 | Reuss et al. |
| 6,366,871 B1 | 4/2002 | Geva |
| 6,377,843 B1 | 4/2002 | Naydenov et al. |
| 6,418,394 B1 | 7/2002 | Puolakanaho et al. |
| 6,433,689 B1 | 8/2002 | Hovind et al. |
| 6,453,164 B1 | 9/2002 | Fuller et al. |
| 6,478,736 B1 | 11/2002 | Mault |
| 6,485,416 B1 | 11/2002 | Platt et al. |
| 6,507,734 B1 | 1/2003 | Berger et al. |
| 6,513,532 B2 | 2/2003 | Mault et al. |
| 6,549,756 B1 | 4/2003 | Engstrom |
| 6,558,320 B1 | 5/2003 | Causey, III et al. |
| 6,579,231 B1 | 6/2003 | Phipps |
| 6,595,929 B2 | 7/2003 | Stivoric et al. |
| 6,600,471 B2 | 7/2003 | Lee et al. |
| 6,605,038 B1 | 8/2003 | Teller et al. |
| 6,612,985 B2 | 9/2003 | Eiffert et al. |
| 6,616,613 B1 | 9/2003 | Goodman |
| 6,636,761 B2 | 10/2003 | Brodnick |
| 6,685,633 B2 | 2/2004 | Albert et al. |
| 6,717,983 B1 | 4/2004 | Toda |
| 6,790,178 B1 | 9/2004 | Mault et al. |
| 6,804,558 B2 | 10/2004 | Haller et al. |
| 6,820,057 B1 | 11/2004 | Loch et al. |
| 6,845,263 B2 | 1/2005 | Kawaguchi |
| 6,893,396 B2 | 5/2005 | Schulze et al. |
| 6,928,535 B2 | 8/2005 | Yamashita et al. |
| 6,950,681 B2 | 9/2005 | Hofmann |
| 6,970,737 B1 | 11/2005 | Brodnick et al. |
| 6,987,965 B2 | 1/2006 | Ng et al. |
| 7,018,339 B2 | 3/2006 | Birnbaum et al. |
| 7,020,508 B2 | 3/2006 | Stivoric et al. |
| 7,031,745 B2 | 4/2006 | Shen |
| 7,061,381 B2 | 6/2006 | Forcier et al. |
| 7,103,407 B2 | 9/2006 | Hjelt et al. |
| 7,107,095 B2 | 9/2006 | Manolas |
| 7,108,659 B2 | 9/2006 | Ross et al. |
| 7,153,262 B2 | 12/2006 | Stivoric et al. |
| 7,162,291 B1 | 1/2007 | Nachaliel |
| 7,162,294 B2 | 1/2007 | Rowlandson et al. |
| 7,188,151 B2 | 3/2007 | Kumar et al. |
| 7,222,054 B2 | 5/2007 | Geva |
| 7,236,818 B2 | 6/2007 | McLeod et al. |
| 7,257,448 B2 | 8/2007 | Crowe et al. |
| 7,260,429 B2 | 8/2007 | Siejko et al. |
| 7,261,690 B2 | 8/2007 | Teller et al. |
| 7,285,090 B2 | 10/2007 | Stivoric et al. |
| 7,319,425 B2 | 1/2008 | Fiorenza et al. |
| 7,324,836 B2 | 1/2008 | Steenstra et al. |
| 7,349,574 B1 | 3/2008 | Sodini et al. |
| 7,351,207 B2 | 4/2008 | Priemer |
| 7,354,400 B2 | 4/2008 | Asafusa et al. |
| 7,382,247 B2 | 6/2008 | Welch et al. |
| 7,383,297 B1 | 6/2008 | Atsmon et al. |
| 7,398,115 B2 | 7/2008 | Lynn |
| 7,415,304 B2 | 8/2008 | Rowlandson et al. |
| 7,444,116 B2 | 10/2008 | Ivanov et al. |
| 7,460,899 B2 | 12/2008 | Almen |
| 7,502,643 B2 | 3/2009 | Farringdon et al. |
| 7,509,159 B2 | 3/2009 | Xue et al. |
| 7,515,043 B2 | 4/2009 | Welch et al. |
| 7,515,044 B2 | 4/2009 | Welch et al. |
| 7,520,860 B2 | 4/2009 | Guion-Johnson et al. |
| 7,542,878 B2 | 6/2009 | Nanikashvili |
| 7,548,623 B2 | 6/2009 | Manabe |
| 7,596,405 B2 | 9/2009 | Kurzweil et al. |
| 7,603,148 B2 | 10/2009 | Michalak |
| 7,647,185 B2 | 1/2010 | Tarassenko et al. |
| 7,654,148 B2 | 2/2010 | Tomlinson, Jr. et al. |
| 7,657,479 B2 | 2/2010 | Henley |
| 7,668,589 B2 | 2/2010 | Bauer |
| 7,689,437 B1 | 3/2010 | Teller et al. |
| 7,701,895 B2 | 4/2010 | Gehasie et al. |
| 7,733,224 B2 | 6/2010 | Tran |
| 7,742,808 B2 | 6/2010 | Nissila et al. |
| 7,806,832 B2 | 10/2010 | Gallagher et al. |
| 7,819,814 B2 | 10/2010 | Gavriely et al. |
| 7,846,104 B2 | 12/2010 | MacQuarrie et al. |
| 7,846,106 B2 | 12/2010 | Andrews et al. |
| 7,904,160 B2 | 3/2011 | Brodnick et al. |
| 7,945,064 B2 | 5/2011 | O'Brien et al. |
| 7,946,959 B2 | 5/2011 | Shum et al. |
| 7,955,273 B2 | 6/2011 | Rahe-Meyer |
| 7,983,749 B2 | 7/2011 | Warren |
| 8,019,609 B2 | 9/2011 | Tamir et al. |
| 8,034,006 B2 | 10/2011 | Celik-Butler et al. |
| 8,062,090 B2 | 11/2011 | Atsmon et al. |
| 8,078,136 B2 | 12/2011 | Atsmon et al. |
| 8,078,278 B2 | 12/2011 | Penner |
| 8,126,526 B2 | 2/2012 | Kitajima et al. |
| 8,126,566 B2 | 2/2012 | Stahmann et al. |
| 8,126,728 B2 | 2/2012 | Dicks et al. |
| 8,130,093 B2 | 3/2012 | Mazar et al. |
| 8,150,750 B2 | 4/2012 | Ray |
| 8,160,276 B2 | 4/2012 | Liao et al. |
| 8,165,677 B2 | 4/2012 | Von Arx et al. |
| 8,216,136 B2 | 7/2012 | Addison et al. |
| 8,224,429 B2 | 7/2012 | Prstojevich et al. |
| 8,265,907 B2 | 9/2012 | Nanikashvili et al. |
| 8,275,553 B2 | 9/2012 | Ochs et al. |
| 8,275,635 B2 | 9/2012 | Stivoric et al. |
| 8,282,550 B2 | 10/2012 | Rasdal et al. |
| 8,285,356 B2 | 10/2012 | Bly et al. |
| 8,301,232 B2 | 10/2012 | Albert et al. |
| 8,301,236 B2 | 10/2012 | Baumann et al. |
| 8,323,188 B2 | 12/2012 | Tran |
| 8,328,718 B2 | 12/2012 | Tran |
| 8,332,233 B2 | 12/2012 | Ott et al. |
| 8,364,250 B2 | 1/2013 | Moon et al. |
| 8,369,936 B2 | 2/2013 | Farringdon et al. |
| 8,374,688 B2 | 2/2013 | Libbus et al. |
| 8,449,471 B2 | 5/2013 | Tran |
| 8,500,636 B2 | 8/2013 | Tran |
| 8,509,882 B2 | 8/2013 | Albert et al. |
| 8,519,835 B2 | 8/2013 | Dunko |
| 8,543,185 B2 | 9/2013 | Yuen et al. |
| 8,548,770 B2 | 10/2013 | Yuen et al. |
| 8,700,137 B2 | 4/2014 | Albert |
| 8,725,229 B2 | 5/2014 | Furue et al. |
| 8,755,871 B2 | 6/2014 | Weng et al. |
| 8,923,958 B2 | 12/2014 | Gupta et al. |
| 8,951,189 B2 | 2/2015 | Osorio |
| 8,951,192 B2 | 2/2015 | Osorio |
| 8,974,396 B1 | 3/2015 | Brady et al. |
| 8,977,347 B2 | 3/2015 | Mestha et al. |
| 9,026,202 B2 | 5/2015 | Albert |
| 9,220,430 B2 | 12/2015 | Albert |
| 9,254,095 B2 | 2/2016 | Galloway et al. |
| 9,351,654 B2 | 5/2016 | Albert |
| 9,420,956 B2 | 8/2016 | Gopalakrishnan et al. |
| 9,572,499 B2 | 2/2017 | Gopalakrishnan et al. |
| 2001/0027384 A1 | 10/2001 | Schulze et al. |
| 2001/0031998 A1 | 10/2001 | Nelson et al. |
| 2001/0051766 A1 | 12/2001 | Gazdzinski |
| 2002/0016541 A1 | 2/2002 | Glossop |
| 2002/0032386 A1 | 3/2002 | Sackner et al. |
| 2002/0072682 A1* | 6/2002 | Hopman ............ A61B 5/0006 600/509 |

(56) References Cited

U.S. PATENT DOCUMENTS

| | | |
|---|---|---|
| 2002/0111556 A1 | 8/2002 | Wegner |
| 2002/0143576 A1 | 10/2002 | Nolvak et al. |
| 2003/0004425 A1 | 1/2003 | Narimatsu et al. |
| 2003/0093002 A1 | 5/2003 | Kuo |
| 2003/0107487 A1 | 6/2003 | Korman et al. |
| 2003/0117987 A1 | 6/2003 | Brebner |
| 2003/0149344 A1 | 8/2003 | Nizan |
| 2003/0187363 A1* | 10/2003 | Alroy .............. A61B 5/0006 600/509 |
| 2003/0193839 A1 | 10/2003 | Singh |
| 2004/0034284 A1 | 2/2004 | Aversano et al. |
| 2004/0044292 A1 | 3/2004 | Yasushi et al. |
| 2004/0059205 A1 | 3/2004 | Carlson et al. |
| 2004/0117212 A1 | 6/2004 | Kong et al. |
| 2004/0120356 A1 | 6/2004 | Davenport et al. |
| 2004/0127802 A1* | 7/2004 | Istvan .............. A61B 5/6841 600/509 |
| 2004/0143403 A1 | 7/2004 | Brandon et al. |
| 2004/0215088 A1 | 10/2004 | Hubelbank |
| 2004/0215094 A1 | 10/2004 | Baumer et al. |
| 2004/0220487 A1 | 11/2004 | Vyshedskiy et al. |
| 2004/0220488 A1 | 11/2004 | Vyshedskiy et al. |
| 2004/0225199 A1 | 11/2004 | Evanyk et al. |
| 2004/0228217 A1 | 11/2004 | Szeto |
| 2004/0236819 A1 | 11/2004 | Anati et al. |
| 2004/0266407 A1 | 12/2004 | Lee et al. |
| 2004/0266480 A1 | 12/2004 | Hjelt et al. |
| 2005/0014531 A1 | 1/2005 | Findikli |
| 2005/0027207 A1 | 2/2005 | Westbrook et al. |
| 2005/0078533 A1 | 4/2005 | Vyshedskiy et al. |
| 2005/0124864 A1 | 6/2005 | Mack et al. |
| 2005/0234353 A1 | 10/2005 | Xue et al. |
| 2005/0239493 A1 | 10/2005 | Batkin et al. |
| 2006/0022833 A1 | 2/2006 | Ferguson et al. |
| 2006/0047215 A1 | 3/2006 | Newman et al. |
| 2006/0173259 A1 | 8/2006 | Flaherty et al. |
| 2006/0190045 A1 | 8/2006 | Marcus et al. |
| 2006/0193270 A1 | 8/2006 | Gehasie et al. |
| 2006/0252999 A1 | 11/2006 | Devaul et al. |
| 2007/0021677 A1 | 1/2007 | Markel |
| 2007/0027386 A1 | 2/2007 | Such et al. |
| 2007/0032731 A1 | 2/2007 | Lovejoy et al. |
| 2007/0063850 A1 | 3/2007 | Devaul et al. |
| 2007/0073266 A1 | 3/2007 | Chmiel et al. |
| 2007/0106133 A1* | 5/2007 | Satchwell .............. A61B 5/0402 600/309 |
| 2007/0106179 A1 | 5/2007 | Bagha et al. |
| 2007/0156060 A1 | 7/2007 | Cervantes et al. |
| 2007/0254604 A1 | 11/2007 | Kim |
| 2007/0265038 A1 | 11/2007 | Kim |
| 2008/0009759 A1 | 1/2008 | Chetham et al. |
| 2008/0058670 A1 | 3/2008 | Mainini |
| 2008/0112885 A1 | 5/2008 | Okunev et al. |
| 2008/0146890 A1 | 6/2008 | Leboeuf et al. |
| 2008/0146892 A1 | 6/2008 | Leboeuf et al. |
| 2008/0171945 A1 | 7/2008 | Dotter |
| 2008/0177162 A1 | 7/2008 | Bae et al. |
| 2008/0198872 A1 | 8/2008 | Pierce |
| 2008/0214903 A1 | 9/2008 | Orbach |
| 2008/0228045 A1 | 9/2008 | Gao et al. |
| 2008/0293453 A1 | 11/2008 | Atlas et al. |
| 2009/0010461 A1 | 1/2009 | Klinghult et al. |
| 2009/0024045 A1 | 1/2009 | Prakash et al. |
| 2009/0037575 A1 | 2/2009 | Crystal et al. |
| 2009/0069642 A1 | 3/2009 | Gao et al. |
| 2009/0117883 A1 | 5/2009 | Coffing et al. |
| 2009/0144080 A1 | 6/2009 | Gray et al. |
| 2009/0149767 A1 | 6/2009 | Rossetti |
| 2009/0156908 A1 | 6/2009 | Belalcazar et al. |
| 2009/0171170 A1 | 7/2009 | Li et al. |
| 2009/0209873 A1 | 8/2009 | Pinter et al. |
| 2009/0273467 A1 | 11/2009 | Elixmann et al. |
| 2009/0279389 A1 | 11/2009 | Irie |
| 2009/0287067 A1 | 11/2009 | Dorogusker et al. |
| 2009/0306485 A1 | 12/2009 | Bell |
| 2009/0312655 A1 | 12/2009 | Lo |
| 2010/0027379 A1 | 2/2010 | Saulnier et al. |
| 2010/0033303 A1 | 2/2010 | Dugan et al. |
| 2010/0035927 A1 | 2/2010 | Ojika et al. |
| 2010/0042008 A1 | 2/2010 | Amitai et al. |
| 2010/0049006 A1 | 2/2010 | Magar et al. |
| 2010/0049037 A1 | 2/2010 | Pinter et al. |
| 2010/0063381 A1 | 3/2010 | Greiser |
| 2010/0069735 A1 | 3/2010 | Berkner |
| 2010/0076276 A1 | 3/2010 | Gilland |
| 2010/0076331 A1 | 3/2010 | Chan et al. |
| 2010/0094152 A1 | 4/2010 | Semmlow |
| 2010/0113950 A1 | 5/2010 | Lin et al. |
| 2010/0148956 A1 | 6/2010 | Song et al. |
| 2010/0184479 A1 | 7/2010 | Griffin, Jr. |
| 2010/0185101 A1 | 7/2010 | Sakai et al. |
| 2010/0204758 A1 | 8/2010 | Boon et al. |
| 2010/0208434 A1 | 8/2010 | Kim et al. |
| 2010/0217099 A1 | 8/2010 | Leboeuf et al. |
| 2010/0217100 A1 | 8/2010 | Leboeuf et al. |
| 2010/0217345 A1 | 8/2010 | Wolfe et al. |
| 2010/0234746 A1 | 9/2010 | Sebelius et al. |
| 2010/0256509 A1 | 10/2010 | Kuo et al. |
| 2010/0256976 A1 | 10/2010 | Atsmon et al. |
| 2010/0281261 A1 | 11/2010 | Razzell |
| 2010/0298711 A1 | 11/2010 | Pedersen et al. |
| 2010/0324378 A1 | 12/2010 | Tran et al. |
| 2010/0331631 A1 | 12/2010 | MacLaughlin |
| 2011/0015496 A1 | 1/2011 | Sherman et al. |
| 2011/0035927 A1 | 2/2011 | Griffin et al. |
| 2011/0060251 A1 | 3/2011 | Verma et al. |
| 2011/0066042 A1 | 3/2011 | Pandia et al. |
| 2011/0117529 A1 | 5/2011 | Barash et al. |
| 2011/0134725 A1 | 6/2011 | Su et al. |
| 2011/0160601 A1 | 6/2011 | Wang et al. |
| 2011/0182445 A1 | 7/2011 | Atsmon et al. |
| 2011/0208076 A1 | 8/2011 | Fong et al. |
| 2011/0235466 A1 | 9/2011 | Booij et al. |
| 2011/0275950 A1 | 11/2011 | Xue et al. |
| 2011/0288425 A1 | 11/2011 | Stewart |
| 2011/0301435 A1 | 12/2011 | Albert et al. |
| 2011/0301439 A1 | 12/2011 | Albert et al. |
| 2012/0021810 A1 | 1/2012 | Terry |
| 2012/0051187 A1 | 3/2012 | Paulson et al. |
| 2012/0053424 A1 | 3/2012 | Kenalty et al. |
| 2012/0071734 A1 | 3/2012 | Shimuta et al. |
| 2012/0083705 A1 | 4/2012 | Yuen et al. |
| 2012/0101396 A1 | 4/2012 | Solosko et al. |
| 2012/0108916 A1 | 5/2012 | Riftine |
| 2012/0123891 A1 | 5/2012 | Patel |
| 2012/0127833 A1 | 5/2012 | Ghen et al. |
| 2012/0143018 A1 | 6/2012 | Skidmore et al. |
| 2012/0147921 A1 | 6/2012 | Conti et al. |
| 2012/0157019 A1 | 6/2012 | Li |
| 2012/0158090 A1 | 6/2012 | Chavan et al. |
| 2012/0171963 A1 | 7/2012 | Tsfaty |
| 2012/0172689 A1 | 7/2012 | Albert et al. |
| 2012/0179056 A1 | 7/2012 | Moulder et al. |
| 2012/0197148 A1 | 8/2012 | Levitan et al. |
| 2012/0285588 A1 | 11/2012 | Sheppard |
| 2012/0289790 A1 | 11/2012 | Jain et al. |
| 2012/0316413 A1 | 12/2012 | Liu et al. |
| 2013/0003852 A1 | 1/2013 | Yamamoto |
| 2013/0030259 A1 | 1/2013 | Thomsen et al. |
| 2013/0085364 A1 | 4/2013 | Lu et al. |
| 2013/0122810 A1 | 5/2013 | Kaufman |
| 2013/0156194 A1 | 6/2013 | Tanioka |
| 2013/0159699 A1 | 6/2013 | Torkkel |
| 2013/0197320 A1 | 8/2013 | Albert et al. |
| 2013/0236980 A1 | 9/2013 | Moretti et al. |
| 2013/0261414 A1 | 10/2013 | Tal et al. |
| 2013/0281816 A1 | 10/2013 | Strauss et al. |
| 2013/0289366 A1 | 10/2013 | Chua et al. |
| 2013/0331663 A1 | 12/2013 | Albert et al. |
| 2014/0050321 A1 | 2/2014 | Albert et al. |
| 2014/0051941 A1 | 2/2014 | Messerschmidt |
| 2014/0051946 A1 | 2/2014 | Arne et al. |
| 2014/0066798 A1 | 3/2014 | Albert |
| 2014/0073969 A1 | 3/2014 | Zou et al. |

(56) References Cited

U.S. PATENT DOCUMENTS

| | | |
|---|---|---|
| 2014/0094707 A1 | 4/2014 | Farringdon et al. |
| 2014/0114166 A1 | 4/2014 | Baxi |
| 2014/0163927 A1 | 6/2014 | Molettiere et al. |
| 2014/0221859 A1 | 8/2014 | Albert |
| 2014/0276162 A1 | 9/2014 | Albert et al. |
| 2015/0018660 A1 | 1/2015 | Thomson et al. |
| 2015/0073285 A1 | 3/2015 | Albert et al. |
| 2015/0087952 A1 | 3/2015 | Albert et al. |
| 2015/0182132 A1 | 7/2015 | Harris et al. |
| 2015/0265164 A1 | 9/2015 | Gopalakrishnan et al. |
| 2015/0297134 A1 | 10/2015 | Albert et al. |
| 2016/0235319 A1 | 8/2016 | Albert |
| 2016/0331247 A1 | 11/2016 | Albert |

FOREIGN PATENT DOCUMENTS

| | | |
|---|---|---|
| CN | 101152081 A | 4/2008 |
| CN | 101828915 A | 9/2010 |
| CN | 201918016 U | 8/2011 |
| CN | 102347804 A | 2/2012 |
| CN | 105338892 A | 2/2016 |
| DE | 2506936 A1 | 9/1976 |
| DE | 4212670 A1 | 1/1994 |
| EP | 0631226 A1 | 12/1994 |
| EP | 1782229 A2 | 5/2007 |
| EP | 1181888 B1 | 9/2007 |
| EP | 1238633 B1 | 10/2008 |
| EP | 2030565 A1 | 3/2009 |
| EP | 2192526 A2 | 6/2010 |
| EP | 2116183 B1 | 2/2012 |
| EP | 2986204 A1 | 2/2016 |
| EP | 3079571 A1 | 10/2016 |
| EP | 3133984 A1 | 3/2017 |
| FR | 2740426 A1 | 4/1997 |
| GB | 2181554 A | 4/1987 |
| GB | 2408105 A | 5/2005 |
| JP | S59122032 A | 7/1984 |
| JP | S59190742 A | 10/1984 |
| JP | S63072231 A | 4/1988 |
| JP | S63294044 A | 11/1988 |
| JP | H01244328 A | 9/1989 |
| JP | H05167540 A | 7/1993 |
| JP | H06326669 A | 11/1994 |
| JP | 2002191562 A | 7/2002 |
| JP | 2002261731 A | 9/2002 |
| JP | 2003010177 A | 1/2003 |
| JP | 2005295378 A | 10/2005 |
| JP | 2006180899 A | 7/2006 |
| JP | 2008532587 A | 8/2008 |
| JP | 2010166961 A | 8/2010 |
| JP | 2012065073 A | 3/2012 |
| KR | 20100059198 A | 6/2010 |
| MX | 2009011781 A | 5/2011 |
| WO | WO-8200910 A1 | 3/1982 |
| WO | WO-8805282 A1 | 7/1988 |
| WO | WO-9008361 A1 | 7/1990 |
| WO | WO-9206551 A1 | 4/1992 |
| WO | WO-9731437 A1 | 8/1997 |
| WO | WO-9838611 A1 | 9/1998 |
| WO | WO-9944494 A1 | 9/1999 |
| WO | WO-0041620 A1 | 7/2000 |
| WO | WO-0147597 A2 | 7/2001 |
| WO | WO-0157619 A2 | 8/2001 |
| WO | WO-02080762 A1 | 10/2002 |
| WO | WO-03075118 A2 | 9/2003 |
| WO | WO-03094720 A1 | 11/2003 |
| WO | WO-2004037080 A1 | 5/2004 |
| WO | WO-2006001005 A2 | 1/2006 |
| WO | WO-2006021956 A2 | 3/2006 |
| WO | WO-2006090371 A2 | 8/2006 |
| WO | WO-2007014545 A2 | 2/2007 |
| WO | WO-2007088315 A1 | 8/2007 |
| WO | WO-2008005015 A1 | 1/2008 |
| WO | WO-2008066682 A2 | 6/2008 |
| WO | WO-2009112976 A1 | 9/2009 |
| WO | WO-2010025166 A1 | 3/2010 |
| WO | WO-2010099066 A2 | 9/2010 |
| WO | WO-2010108287 A1 | 9/2010 |
| WO | WO-2010113354 A1 | 10/2010 |
| WO | WO-2010144626 A1 | 12/2010 |
| WO | WO-2011006356 A1 | 1/2011 |
| WO | WO-2011008838 A1 | 1/2011 |
| WO | WO-2011014292 A1 | 2/2011 |
| WO | WO-2011022942 A1 | 3/2011 |
| WO | WO-2011040877 A1 | 4/2011 |
| WO | WO-2011040878 A1 | 4/2011 |
| WO | WO-2011113070 A1 | 9/2011 |
| WO | WO-2011137375 A2 | 11/2011 |
| WO | WO-2011156374 A2 | 12/2011 |
| WO | WO-2012046158 A1 | 4/2012 |
| WO | WO-2012108895 A1 | 8/2012 |
| WO | WO-2012129413 A1 | 9/2012 |
| WO | WO-2012160550 A1 | 11/2012 |
| WO | WO-2013028960 A1 | 2/2013 |
| WO | WO-2013036307 A1 | 3/2013 |
| WO | WO-2013066642 A1 | 5/2013 |
| WO | WO-2013093690 A1 | 6/2013 |
| WO | WO-2013122788 A1 | 8/2013 |
| WO | WO-2013138500 A1 | 9/2013 |
| WO | WO-2013155196 A2 | 10/2013 |
| WO | WO-2013192166 A1 | 12/2013 |
| WO | WO-2014172451 A1 | 10/2014 |
| WO | WO-2016183515 A1 | 11/2016 |

OTHER PUBLICATIONS

Australian Design Awards. Heartplus Micro; printed from website http://www.designawards.com/au; printed on Apr. 12, 2002 • 6 pages.

Bajaj, M.D.; "Event Recording in Ambulatory Patients with Syncopal Events"; University of Kansas; Wichita, Kansas; (no date); pp. 15-18; printed on or before Apr. 14, 2010.

Bluetooth. Headset Profile (HSP), printed from website http://bluetooth.com/English/Techmology/Works/Pates/HSP.asgx, printed on May 12, 2010, 1 Page.

Bramanti et al., Multichannel telemetric system for biomedical signals via switched telephone lines, Medical and Biological Engineering and Computing, Sep. 1982, vol. 20, No. 5, pp. 653-656.

Burke, A Micropower Dry-Electrode ECG Preamplifier, IEEE Transactions on Biomedical Engineering, Feb. 2000, vol. 47, No. 2, pp. 155-162.

Card Guard CG-6108 ACT Ambulatory Cardiac Telemetry Brochure; Card Guard; The Telemedicine Company: Switzerland; 2006; 2 pages.

Cardiocomm Solutions; GEMS Air. (PC based ECG management) printed from website http://www.cardiocommsolutions/com; printed on Mar. 19, 2010; 1 page.

Carpenter and Frontera, Smart-watches: a potential challenger to the implantable loop recorder? Europace, 18:791-793, 2016.

Charuvastra. Transtelephonic Cardiac Event Recording for Arrhythmia Surveillance; printed from website http://tchin.org/resource room/c art• printed on Mar. 26, 2010• 2 pages.

Cheng, Allen C.; "Real-Time Cardiovascular Diseases Detection on a Smartphone"; Departments of Electrical And Computer Engineering, Bioengineering, Neurological Surgery and Computer Science; University of Pittsburgh; Pittsburgh, PA; printed on or before Apr. 14, 2010, 2 pages.

Chinese Patent Application No. 2013800135500 First Office Action dated Oct. 20, 2015.

Creative. PC-80B Portable ECG Monitor w/sd card extension slot; printed from website www.amazon.com/Portable-Monitor-extension-leather-shipping/dp/B0010jWKUE; printed on Feb. 4, 2010• 5 pages.

Deveau, "Health Care eyes smart phones to heal ills", printed from the website http://www.theQiobeandmail.com on Sep. 17, 2009, 4 pages.

Dinh. Heart activity monitoring on smartphone. IPCBEE—Int conf Biomedical Eng and Technol. Jun. 17-19, 2011. 11:45-49.

(56) References Cited

OTHER PUBLICATIONS

Dobrev, et al., Bootstrapped two-electrode biosignal amplifier, Med Bioi Eng Comput, 2008, 7 pages.
Dolan; Qualcomm launches ECG smartphone program in China; Sep. 8, 2011; 11 pgs.; retrieved Mar. 19, 2014 from the internet (http://mobihealthnews.com/13092/qualcomm-launches-ecg-smartphone-program-in-china/).
Elert, Glenn (Editor); Frequency Range of Human Hearing; The Physics Factbook; web version as of Mar. 29, 2010; 2 pgs.; printed Jun. 6, 2012 (http://web.archive.org/web/20100329141847/http:1/hypertextbook.com/facts/2003/ChrisDAmbrose.shtml).
EPI Life phone sports ECG function, can let doctors know if you're not gonna make it; printed from website http://www.engadget.com/2010/06/16/epi-life-phonesports:printed on Jun. 17, 2010• 4 pages.
European Patent Application No. 11793020.6 extended European Search Report dated Jan. 10, 2017.
European Patent Application No. 11865699.0 Communication dated Dec. 19, 2016.
European Patent Application No. 14785223.0 extended European Search Report dated Aug. 23, 2016.
European Patent Application No. 11865699.0. search report and written opinion dated Nov. 21, 2014.
Favorite Plus. Handheld Easy ECG Monitor—Handheld Easy EKG Monitor; printed from website www.favoriteplus.com/easy-ecg-handgeld-monitor-fp; printed on Feb. 4, 2010; 2 pages.
Favorite Plus. Handheld ECG Monitor—Handheld EKG Monitor at Favoriteplus.com; printed from website www.favoriteplus.com/handheld-ecg-ekg-monitor; printed on Feb. 4, 2010; 3 pages.
Favorite Plus. Handheld ECG Monitor—Handheld EKG Monitor InstantCheck; printed from website http://www. favoriteplus.com/instanchcheck-hand held-ecg-ekg-monitor; printed on Feb. 4, 2010; 2 pages.
Ferrick, M.D.; Holter Monitoring and cardiac Event Recording in Assessing Symptomatic Patient; Albert Einstein College of Medicine; Bronx, New York; (no date)• pp. 11-14• printed on or before Apr. 14, 2010.
Free2Move. Vitaphone 2300; www.free2move.us/News/NewsVitaghone 240105.htm printed May 12, 2010.
Fulford-Jones, et al., "A Portable, Low-Power, Wireless Two-Lead EKG System", Division of Engineering and Applied Sciences, Harvard University, Sep. 2004, 4 pages.
Garabelli et al. Accuracy and Novelty of an Inexpensive iPhone-based Event Recorder (Presentation Poster/Abstract) Heart Rhythm 2012, 33rd Annual Scientific Session. SP23. Innovation Poster Session II. No. IA02-1; May 11, 2012.
GBI Portal. Qualcomm's wireless reach mHealth project to improve cardiovascular disease in resource scarce China; Feb. 17, 2012; 7 pgs. Retrieved Mar. 19, 2014 from www.intergrallc.com/2012/02/17/qualcooms-wireless-reach-mhealth-project-to-improve-cardiovascular-disease-in-resource-scarce-china/.
GE Healthcare., "Marquette heart rate turbulence analysis program", 2005, DC-0160-12.05-EN-US. 4 pages.
Gillette, M.D.; "Diagnosis of Pediatric Arrhythmias with Event Recording"; Medical University of South Carolina; Charleston, South Carolina; (no date); pp. 25-32; printed on or before Apr. 14, 2010.
Grier, James W.; "How to use 1-lead ECG recorders to obtain 12-lead resting ECGs and exercise ("stress") ECGs"; Department of Biological Sciences: printed from website http://www.ndsu.edu/pubweb/rvgrier; printed on Jun. 7, 2010; 13 pages.
Hannaford, Kat; "How To Turn Your iPhone Into A Laser, Fan or Flashlight"; printed from website htto://m.qizmodo.com/5534904• printed on Feb. 3, 2011, 2 pages.
Hartmann, "ECG Front-End Design is Simplified with MicroConverter" AnalogDialogue, Nov. 2003, vol. 37, pp. 1-5.
Hayes, M.D.; "Approaches to Diagnosing Transient Arhythmias" An Overview; Mayo Clinic; Rochester Minnesota; (no date); pp. 7-10; printed on or before Apr. 14, 2010.
Hearing Loss Assoc. of Kentuckiana; Decibal Ratings/Hazardous Time Exposures of Common Noise (excerpt from Survivor's Manual); web version as of Oct. 5, 2008; 2 pgs.; printed Jun. 6, 2012 (http://web.archive.org/web/20081005143856/http://www.hearinglossky.orglhlasurvival1.html).
Huang, Tina; Age-related hearing loss; Minnesota Medicine; 90(10); pp. 48-50; Oct. 2007; printed Jun. 6, 2012 from: http://www.minnesotamedicine.com/PastIssues/PastIssues2007/0ctober2007/Ciinca1Huang0ctober2007.aspx).
IMEC News; IMEC extends flexible ECG patch to enable arrhythmia detection; printed from website http://www2.imec.be/imeC' printed on Aug. 18, 2009 1 page.
Instromedix. Cardiac Event Recording FAQ's; Instromedix A Card Guard Company, San Diego, CA.; printed from website www.instromedix.com/pdf/products/cardiac; printed on or before Apr. 14, 2010.
Instromedix. The Arrhythmia Monitoring System; King of Hearts Express AF Recorder Brochure from Instromedix• A CardGuard Company; Rosemont IL; 2004• 3 pages.
International preliminary report on patentability dated Jul. 29, 2014 for PCT/US2013/023370.
International search report and written opinion dated Feb. 12, 2015 for PCT/US2014/054414.
International search report and written opinion dated Feb. 17, 2012 for PCT/US2011/039445.
International search report and written opinion dated Apr. 27, 2012 for PCT/US2011/053708.
International search report and written opinion dated Apr. 30, 2015 for PCT/US2014/070170.
International search report and written opinion dated May 15, 2013 for PCT/US2013/023370.
International search report and written opinion dated Dec. 17, 2013 for PCT/US2013/055458.
International search report dated Sep. 1, 2014 for PCT/US2014/034350.
International search report dated Dec. 10, 2013 for PCT/US2013/057576.
Japanese Patent Application No. 2014-511335 Decision of Rejection dated Jul. 28, 2016.
Japanese Patent Application No. 2014-554916 Office Action dated Sep. 26, 2016.
Jenkins II, W.; Time/Frequency Relationships for an FFT-Based Acoustic Modem; Naval Postgraduate School; pp. 1-102; Sep. 2010 (http://edocs.nps.edu/npspubs/scholarly/theses/2010/Sep/1 OSep_Jenkins.pdf) printed Oct. 2, 2013
Kim, et al., "Detection of Atrial Fibrillation Episodes using Multiple Heart Rate Variability Features in Different Time Periods." Conference Proceedings IEEE Eng Med Biol Soc EMBS, 30th Annual International Conference, Aug. 20-25, 2008, p. 5482-5485.
Koerner. The Author's Metrics; Wired Magazine Article; New York, NY; Jul. 2009; p. 93-126.
Kumar, M.D., "Zio Patch", printed from website http://www.irhythmtech.com/zio-solution/zio-gach/, grinted on Apr. 12, 2010.
Kumparak, Greg; "Visa officially announces their case that turns your iPhone into a credit card (and we've got pies!)"; May 17, 2010; printed from website www.mobilecrunch.com• printed on Feb. 3, 2011.
Lau, et al. iPhone ECG application for community screening to detect silent atrial fibrillation: A novel technology to prevent stroke. Int J Cardiol. Apr. 30, 2013;165(1):193-4.
Lau, et al. Performance of an Automated iPhone ECG Algorithm to Diagnose Atrial Fibrillation in a Community AF Screening Program (SEARCH-AF). Heart, Lung and Circulation. 2013; 22:S205.
Lau et al. Validation of an iPhone ECG application suitable for community screening for silent atrial fibrillation—A novel way to prevent stroke (Presentation Abstract 16810); American Heart Association 2012 Scientific Sessions and Resuscitation Science Symposium; 126(1); Nov. 20, 2012, 2 pages.
Leijdekkers et al., "Trial Results of a Novel Cardiac Rhythm Management System using Smart Phones and wireless ECG Sensors", Proceedings ofthe International Conf. On Smart homes and health Telematics., Jul. 1-3, 2009, Tours, France, 8 pages.
Levkov et al., "Removal of power-line interference from the ECG: a review of the subtraction procedure" BioMedical Engineering (56) References Cited

OTHER PUBLICATIONS

Online 2005, printed from website http://www.biomedical-engineeringonline.com/contenU4/1/50 pp. 1-18.
Lin; et al., An intelligent telecardiology system using a wearable and wireless ECG to detect atrial fibrillation. May 2010, 14(3), 726-33.
Lowres, et al. Screening Education And Recognition in Community pHarmacies of Atrial Fibrillation to prevent stroke in an ambulant population aged =65 years (SEARCH-AF stroke prevention study): a cross-sectional study protocol. BMJ Open. Jun. 25, 2012; 2(3)e001355.
M Med Choice. Handheld ECG Monitor Brochure; M Med Choice, Beijing Choice Electronic Technology Co. LTD.• published on or before Apr. 14, 2010, 6 pages.
M Med Choice. Handheld ECG Monitor MD100A1; printed from website http://www.choicemmed.com/productshow.as_p; printed on Dec. 28, 2009; 2 pages.
M Med Choice. Handheld ECG Monitor MD100B; printed from website http://www.choicemmed.com/productshow.asp; printed on Dec. 28, 2009• 2 pages.
M Med Choice printed from website http://www.choicemmed.con/1xwm .asp; printed on Dec. 28, 2009• 1 page.
MacFarlane, et al. Resting 12-lead ECG electrode placement and associated problems; SCST update 1995; 15pgs. Printed Feb. 18, 2014 from www.scst.org.uk/resources/RESTING_12.pdf.
Mauvila ECG Tutorial; Basic ECG Interpretation Tutorial; Sections 1-12; printed from website http://mauvila.com/ECG/ecg.htm• printed on Mar. 26, 2010• 56 pages.
MedGadget. Zio Patch Wins Medical Design Award.MedGadget internet journal of emerging medical technologies, 2010, 1 page, printed from website: http://medaadaet.com/archives/2010/04/zio_patch_wins_medial_design_award_1.html.
MiCardioMobile: Remote Wireless Cardiac Rehabilitation Monitoring printed from website htto://alivetec.cable.nu/cardiomobile• printed on or before Apr. 14, 2010, 1 page.
Mobility Mind. Use your Treo 650 as a portable ECG monitoring device, Mobility Mind Celebrating mobile Internet lifestyle and culture, Sep. 14, 2005, 1 page. printed from website http://www.treotoday.net/2005/09/14/use-your-treo-650-as-a-portab le-ecg-monitoring-device/.
Modem Protocols Explained; ftp://kermit.columbia.edu/kermit/cu/protocol.html; 5 pgs.; printed Oct. 2, 2013.
Modem Tutorial; http://www.lsu.edu/OCS/its/unix/tutoriai/ModemTutoriai/ModemTutorial.html; 2 pgs.; printed Oct. 2, 2013.
Muench, Frederick, PhD; "HRV: The Manurfacturers and Vendors Speak; The portable StressEraser Heart Rate Variability Biofeedback Device: Background and Research"• Biofeedback vol. 36 Issue 1, pp. 35-39• published Spring 2008.
Murph. RedEye mini converts iPhone, iPad or iPod touch into IR-beaming universal remote. printed from website http://www.engadget.com/2010/03/02/redeye; printed on Mar. 2, 2010; 3 pages.
Nam et al.; An Ultrasonic Sensor Based Low-Power Acoustic Modem for Underwater Communication in Underwater Wireless Sensor Networks; Computer Network Lab, Dept. of Elec. Eng., Korea Univ.; pp. 494-504; Dec. 2007 (http://nesl.ee.ucla.edu/fw/torres/home/Dropbox/good_paper_mico_controller.pdf; 11 pgs.; printed Oct. 2, 2013).
Neuroreille; Audiometry; web version as of Oct. 14, 2008; 1 pg.; printed Jun. 6, 2012 (http://www.neuroreille.com/promenade/english/audiometry/audiometry.htm).
New Professional Quality ECGEKG Portable Heart Monitor; printed from website http://cgibay.com/ws/eBayiSAPI.dll• printed on Feb. 4, 2010• 3 pages.
Notice of allowance dated Jan. 8, 2014 for U.S. Appl. No. 14/015,303.
Notice of allowance dated Jan. 27, 2014 for U.S. Appl. No. 14/015,303.
Notice of allowance dated Feb. 26, 2014 for U.S. Appl. No. 14/015,303.
Notice of allowance dated May 23, 2014 for U.S. Appl. No. 13/108,738.
Notice of allowance dated Jul. 9, 2013 for U.S. Appl. No. 12/796,188.
Notice of allowance dated Aug. 28, 2012 for U.S. Appl. No. 13/420,520.
Notice of allowance dated Dec. 4, 2013 for U.S. Appl. No. 14/015,303.
Notice of Allowance dated Mar. 29, 2016 for U.S. Appl. No. 14/254,310.
Office action dated Jan. 2, 2014 for U.S. Appl. No. 13/108,738.
Office action dated Jun. 18, 2012 for U.S. Appl. No. 13/420,520.
Office action dated Sep. 12, 2014 for U.S. Appl. No. 13/108,738.
Office action dated Oct. 6, 2014 for U.S. Appl. No. 14/252,044.
Office action dated Oct. 29, 2012 for U.S. Appl. No. 12/796,188.
Office action dated Nov. 19, 2014 for U.S. Appl. No. 13/969,446.
Office Action dated Aug. 25, 2015 for U.S. Appl. No. 14/479,105.
Office Action dated Dec. 21, 2015 for U.S. Appl. No. 13/964,490.
Office Action dated Feb. 24, 2016 for U.S. Appl. No. 14/730,122.
Office Action dated Jun. 13, 2016 for U.S. Appl. No. 14/730,122.
Office Action dated May 18, 2015 for U.S. Appl. No. 13/752,048.
Omron Portable ECG EKG Handheld HCG-801 Monitor; printed from website http://www.amazon.com/Omron-Portable-Handheld-HCG-801-Monitor/dp/B0019WH3EO• printed on Feb. 24, 2010• 5 pages.
Omron Portable ECG Monitor; printed from website http://www.target.com/gp/detail.html; printed on Mar. 26, 2010• 1 page.
Oresko, et al., "Detecting Cardiovascular Diseases via Real-Time Electrocardiogram Processing on a Smartphone", 2009 Workshop on Biomedicine in Computing: Systems, Architectures, and Circuits, pp. 13-16.
PCT/US2014/070170 International Preliminary Report on Patentability dated Jun. 23, 2016.
PCT/US2014/054414 International Preliminary Report on Patentability dated Mar. 17, 2016.
PCT/US2016/032524 International Search Report and Written Opinion dated Aug. 19, 2016.
Perez, Sarah; No NFC? No Problem; New Startup Zoosh Provides Workaround Technology (Jun. 20, 2011 ); printed on or before Jun. 27, 2011 from website; 2 pgs.; (http://www.readwriteweb.com/archives).
Prystowsky, M.D.; "Chairmans Introduction"; Duke University Medical Center; Indianapolis, Indiana• (no date)• pp. 5-6• printed on or before Apr. 14, 2010.
Prystowsky, M.D.; "Chairmans Summary"; Duke University Medical Center; Indianapolis Indiana; (no date); pp. 39-40• printed on or before Apr. 14, 2010.
Prystowsky, M.D., "The Clinical Application, Diagnostic Yield and Cost Considerations of Cardiac Event Recorders", Indianapolis, Indiana (no date) pp. 19-23. printed on or before Apr. 14, 2010.
Puurtinen, et al., Best Electrode Locations for a Small Bipolar ECG Device: Signal Strength Analysis of Clinical Data, Annals of Biomedical Engineering, vol. 37, No. 2, Feb. 2009 (© 2008) pp. 331-336.
Raju Heart-Rate and EKG Monitor Using the MSP430FG439, SLAA280—Oct. 2005—Revised Sep. 2007, 11 pages.
Read-My-Heart. ECG Machine Handheld Read MyHeart; (product item No. HH-3413) printed from website http://www.helioliving.com/ECG-Machi ne-Handheld-ReadMyHea rt; printed on Feb. 4, 2010; 1 page.
Readmyheart Personal Handheld ECG Monitor with Free Illustrator Book & Free Electrodes V2.2; printed from website http://www.amazon.com/Readmyheart-Personai-Handheld-illustrator-Eiectrodes/dp/B0010AN63W; printed on Mar. 26, 2010; 4 pages.
Ricker. Square payment dongle demoed for iPhone toting hippies and you (video); printed from website http://www.engadget.com/2010/01/18/square-payment; printed on Jan. 18, 2010; 6 pages.
Rockwood. The Networked Body Magazine Article from Fast Talk Magazine; Jul./Aug. 2009; pp. 19-26.
Salahuddin, et al., "Ultra Short Term Analysis of Heart Rate Variability using Normal Sinus Rhythm and Atrial Fibrillation ECG Data", Engineering in Medicine and Biology Society, Aug. 2007, pp. 4656-4659.
Saxon, et al. iPhone rhythm strip—the implications of wireless and ubiquitous heart rate monitoring. JACC; 59(13): E726; Mar. 2012.
Saxon. Ubiquitous Wireless ECG Recording: A Powerful Tool Physicians Should Embrace. J Cardiovasc Electrophysiol. 24(4): pp. 480-483; Apr. 2013.

(56) References Cited

OTHER PUBLICATIONS

Semler, M.D.; "The Future of Cardiac Event Monitoring"; St. Vincent Hospital and Medical Center; Portland Oregon; (no date); pp. 33-37; printed on or before Apr. 14, 2010.

SFO Medical. Choice Portable Handheld ECG EKG Monitor; printed from website http://www.amazon.com/Choice-Portable-Handheld-ECG-Monitor/dp/B001Q74VOM; printed on Mar. 26, 2010; 1 page.

Shenzhen New Element Med. Equipment. Wireless ECG Monitoring System, printed from website http://www.alibaba.com/product-gs/248168581/Wireless_ECG_Monitoring_system.html., printed on Mar. 26, 2010, 2 pages.

Shumaker, J.; Designing an Ultrasonic Modem for Robotic Communications; Army Research Laboratory; 26 pgs.; Mar. 2009 (http://www.dtic.mil/cgi-bin/GetTRDoc?AD=ADA499556) printed Oct. 2, 2013.

Smith. Smartphone may keep the cardiologist away, The Independent, Health & Families, Mar. 5, 2010, printed from website http://www.independent.co.uk/life-style/health-and-families/healthnews/smartghone-may-keep-the-cardiologist-away-1916652.html, printed on Mar. 26, 2010.

Stevens, "Apple's Seamlessly Embedded Heart Rate Monitor could turn the iPhone into a new-age mood ring", printed from the website http://www.enaadaet.com on May 6, 2010, 3 pages.

Taleb Medical. Observer Hand-held ECG Monitor MD100B; (no date); printed on or before Apr. 14, 2010, 1 page.

Tei, et al., New index of combined systolic and diastolic myocardial performance: a simple and reproducible measure of cardiac function—a study in normals and dilated cardiomyopathy; J Cardiol.; 26(6):357-366; Dec. 1995.

Texas Instruments. Information for Medical Applications, "Biophysical Monitoring-Electrocardiogram (ECG) Front End", Apr. 2004, 2 pages.

Tschida. Power A's New Case Turns Your iPhone Into A Universal Remote; printed from website http://appadvice.com/appnn; printed on Mar. 1, 2010• 2 pages.

U.S. Appl. No. 13/964,490 Notice of Allowance dated Jan. 6, 2017.
U.S. Appl. No. 14/479,105 Office Action dated Jul. 22, 2016.
U.S. Appl. No. 14/494,191 Office Action dated Jul. 20, 2016.
U.S. Appl. No. 14/730,122 Notice of Allowance dated Dec. 6, 2016.
U.S. Appl. No. 15/140,072 Office Action dated Dec. 23, 2016.
U.S. Appl. No. 15/154,849 Office Action dated Feb. 17, 2017.

Vanhemert, Kyle; "XWave Headset Lets You Control iPhone Apps With Your Brain"; Sep. 8, 2010; printed from website http://gizmodo.com; printed on Sep. 8, 2010, 4 pages.

Vitaphone. Telemedicine since 1999: Modern health management is our special subject. 3 pgs. Retrieved Mar. 19, 2014 from www.vitaphone.de/en/company/history-of-vitaphone/.

Wikimedia Laboratories; Acoustics; web archive version dated Jan. 25, 2009; 2 pgs.; printed Jun. 6, 2012 (http://liveweb.archive.org/http://en.labs.wikimedia.org/wiki/Acoustics).

Wikipedia; Aliasing; web version as of Apr. 3, 2011; S pgs.; printed Jun. 6, 2012 (http://liveweb.archive.org/http://en.wikipedia.org/w/index.php?title=Aiiasing&oldid=422141882).

Wikipedia; Hearing Range; web version as of Feb. 6, 2010; 5 pgs.; printed Jun. 6, 2012 (http://web.archive.org/web/201 002062137 41/http://en.wikipedia.org/wiki/Hearing_range).

Wikipedia ."Pulse oximetry", printed from website httg://en.wikigedia.orq on May 10, 2010, 4 pages.

Wisneski, C.; Ultrasonic Local Area Communication; http://alumni.media.mit.edu/-wiz/ultracom.html; 2 pgs.; printed Oct. 2, 2013.

Woodward et al; "Bio-Potential-To-Frequency Converter/Modulator"; Electronic Design• Aug. 1999• p. 117.

Ziegler, Chris; "EPI Life phone sports ECG function, can let doctors know if you're gonna make it"; printed from website www.enoadoet.com/2010/06/; Jun. 17, 2010,3 pages.

Chinese Patent Application No. 2014800331017 Office Action dated May 16, 2017.

European Patent Application No. 14869033.2 extended European Search Report dated Jul. 5, 2017.

U.S. Appl. No. 14/479,105 Office Action dated Jun. 1, 2017.
U.S. Appl. No. 14/692,563 Office Action dated Jun. 29, 2017.

* cited by examiner

HEART MONITORING SYSTEM USABLE WITH A SMARTPHONE OR COMPUTER

CROSS REFERENCE TO RELATED APPLICATIONS

This application is a continuation of U.S. patent application Ser. No. 13/964,490, filed Aug. 12, 2013, titled "HEART MONITORING SYSTEM USABLE WITH A SMARTPHONE OR COMPUTER," issued as U.S. Pat. No. 9,649,042 on May 16, 2017, which is a divisional of U.S. patent application Ser. No. 12/796,188, filed Jun. 8, 2010, titled "HEART MONITORING SYSTEM USABLE WITH A SMARTPHONE OR COMPUTER," issued as U.S. Pat. No. 8,509,882 on Aug. 13, 2013, which are herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

STATEMENT REGARDING FEDERALLY SPONSORED RESEARCH OR DEVELOPMENT

Not applicable.

BACKGROUND

1. Field of Invention

The presently claimed and disclosed inventive concept(s) relates generally to personal physiology monitoring devices and methods and, more particularly, but not by way of limitation, to devices, systems and software for providing ECG, heart rate and cardiac arrhythmia monitoring utilizing a computing device such as a smartphone.

2. Background of the Invention

The prior art includes numerous systems wherein ECG data or the like is monitored and/or transmitted from a patient to a particular doctor's office or health service center. For example, U.S. Pat. No. 5,735,285 discloses use of a handheld device that converts a patient's ECG signal into a frequency modulated audio signal that may then be analyzed by audio inputting via a telephone system to a selected handheld computer device or to a designated doctor's office. Similarly, U.S. Pat. No. 6,264,614 discloses a heart monitor, which is manipulated by the patient to sense a biological function such as a heart beat, and outputs an audible signal to a computer microphone. The computer processes the audible signal and sends resulting data signals over a network or Internet. U.S. Pat. No. 6,685,633 discloses a heart monitor that a patient can hold against his or her chest. The device outputs an audible signal responsive to the function or condition, such as the beating of the heart, to a microphone connected to a computer.

U.S. Pat. App. Publication No. 20100113950 discloses an electronic device having a heart sensor including several leads for detecting a user's cardiac signals. The leads are coupled to interior surfaces of the electronic device housing to hide the sensor from view. Using the detected signals, the electronic device can then identify or authenticate the user.

Limitations of the prior art utilizing acoustic signals include a signal to noise ratio that is diminished by talking or any other noisy activity in the vicinity, thus potentially jeopardizing the integrity of the heart monitoring data signals. Additionally, the audible signals can be heard by anyone in the vicinity of the computer and heart monitor, which can be bothersome to the user as well as to others in the vicinity. Other applications fail to provide a reliable, inexpensive personal monitoring device that is readily compatible with existing computing devices such as smartphones. It would be advantageous if these issues were addressed in a personal monitoring device transmitting real time physiological data.

SUMMARY OF THE INVENTION

Embodiments of the presently claimed and disclosed invention are directed to a personal monitoring device having a sensor assembly configured to sense physiological signals upon contact with a user's skin. The sensor assembly produces electrical signals representing the sensed physiological signals. A converter assembly, integrated with, and electrically connected to the sensor assembly, converts the electrical signals generated by the sensor assembly to a frequency modulated physiological audio signal. In one embodiment, the frequency modulated physiological audio signal has a carrier frequency in the range of from about 6 kHz to about 20 kHz.

In another embodiment, the personal monitoring device includes a cable connected to the converter assembly for transmitting the frequency modulated physiological audio signal to a 3.5 mm headphone jack on a smartphone, wherein the converter assembly is electrically isolated from the smartphone by an audio isolation transformer. In this case, the frequency modulated physiological audio signal has a carrier frequency in the range of from about 1 kHz to about 20 kHz.

In yet another embodiment, the personal monitoring device includes a wireless radio transmitter configured to utilize Bluetooth® headset technology to transmit the frequency modulated physiological audio signal, having a carrier frequency in the range of from about 1 kHz to about 20 kHz, to a Bluetooth® enabled computing device.

An ECG device of the presently claimed and disclosed inventive concept(s) includes an electrode assembly configured to sense heart-related signals upon contact with a user's skin, and to convert the sensed heart-related signals to an ECG electric signal. A converter assembly, integrated with, and electrically connected to the electrode assembly, is configured to convert the electric ECG signal generated by electrode assembly to a frequency modulated ECG audio signal having a carrier frequency in the range of from about 6 kHz to about 20 kHz.

In one embodiment, a smartphone protective case, usable as an ECG device, is provided. An electrode assembly, configured to sense heart-related signals upon contact with a user's skin, and to convert the sensed heart-related signals to an ECG electric signal, is provided. A converter assembly, integrated with, and electrically connected to the electrode assembly, is configured to convert the electric ECG signal generated by the electrode assembly to a frequency modulated ECG audio signal having a carrier frequency in the range of from about 6 kHz to about 20 kHz, and further configured to output the ECG audio signal through an audio transmitter at a signal strength capable of being received by a smartphone positioned within the smartphone protective case.

In a second embodiment, an ECG device is provided in a housing having an electrode assembly configured to sense heart-related signals upon contact with a user's skin, and to convert the sensed heart-related signals to an ECG electric signal. A converter assembly integrated with, and electrically connected to the electrode assembly, is configured to convert the electric ECG signal generated by electrode assembly to a frequency modulated ECG audio signal having a carrier frequency in the range of from about 6 kHz to about 20 kHz, and further configured to output the ECG audio signal through an audio transmitter at a signal strength capable of being received by a smartphone located near the ECG device.

In another embodiment, an ECG device is provided having an electrode assembly configured to sense heart-related signals upon contact with a user's skin, and to convert the sensed heart-related signals to an ECG electric signal. A converter assembly integrated with, and electrically connected to the electrode assembly, is configured to convert the electric ECG signal generated by electrode assembly to a frequency modulated ECG audio signal. A cable is provided for transmitting the frequency modulated ECG audio signal to a 3.5 mm headphone jack on a smartphone, wherein the converter assembly is electrically isolated from the smartphone by an audio isolation transformer.

In yet another embodiment, a computer-readable storage medium is provided for storing a set of instructions capable of being executed by one or more computing devices, causing the one or more computing devices to digitize and demodulate a frequency modulated ECG audio signal having a carrier frequency in the range of from about 6 kHz to about 20 kHz to produce real time demodulated digital ECG data, and to display on a display screen of the computing device, the real time ECG signal represented by the demodulated digital ECG data.

Thus, utilizing (1) the technology known in the art; (2) the above-referenced general description of the presently claimed and disclosed inventive concept(s); and (3) the detailed description of the invention that follows, the advantages and novelties of the presently claimed and disclosed inventive concept(s) would be readily apparent to one of ordinary skill in the art.

DETAILED DESCRIPTION OF THE INVENTION

Before explaining at least one embodiment of the invention in detail, it is to be understood that the invention is not limited in its application to the details of construction, experiments, exemplary data, and/or the arrangement of the components set forth in the following description. The invention is capable of other embodiments or of being practiced or carried out in various ways. Also, it is to be understood that the terminology employed herein is for purpose of description and should not be regarded as limiting.

Figure 1:
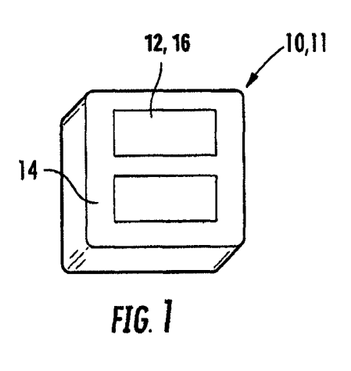
FIG. 1 is a schematic representation of an embodiment of a personal monitoring device of the present invention.
Figure 2:
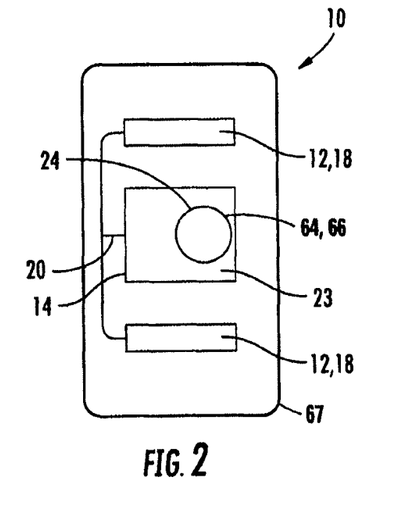
FIG. 2 is a schematic representation of another embodiment of a personal monitoring device of the present invention.

The presently claimed and disclosed inventive concepts provide a personal monitoring device 10, embodiments of which are shown schematically in FIGS. 1 and 2. The acquisition electronics 11 of the monitoring device 10 includes a sensor assembly 12 configured to sense physiological signals upon contact with a user's skin. The sensor assembly 12 produces electrical signals representing the sensed physiological signals, which input to a converter assembly 14, integrated with the sensor assembly 12. Converter assembly 14 converts the electrical signals generated by the sensor assembly 12 to a frequency modulated physiological audio signal having a carrier frequency in the range of from about 1 kHz to about 20 kHz. In one embodiment, the frequency modulated physiological audio signal has a carrier frequency in the range of from about 6 kHz to about 20 kHz.

The sensor assembly 12 can include any suitable sensor operative to detect a physiological signal that a user desires to monitor. Nonlimiting examples of such physiological signals include, but are not limited to, respiration, heart beat, heart rate, electrocardiogram (ECG), electromyogram (EMG), electrooculogram (EOG), pulse oximetry, photoplethysmogram (PPG) and electroencephalogram (EEG).

Figure 3:
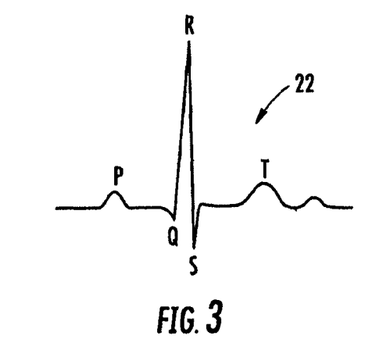
FIG. 3 is an example of graphical ECG representation.

A respiration detector can be a conventional microphone assisted stethoscope 16. Heart beat and heart rate can be detected as well using a conventional microphone assisted stethoscope 16, or by using an electrode assembly 18 to sense electrical signals generated by the heart over time. Such electrodes 18 can also be used to detect the electrical activity of the heart over time for electrocardiography (ECG). An ECG is a measurement of the small electrical changes on the skin generated when the heart muscle depolarizes during each heart beat. The output from a pair of electrodes 18 is known as a lead 20. Small rises and falls in the voltage between two electrodes placed on either side of the heart can be processed to produce a graphical ECG representation 22 such as the example ECG shown in FIG. 3.

Electromyography (EMG) detects the electrical potential generated by muscle cells when the cells are electrically or neurologically activated. The signals can be analyzed to detect medical abnormalities. Electrooculography (EOG) is a technique for measuring the resting potential of the retina. Usually, pairs of electrodes 18 are placed either above and below the eye, or to the left and right of the eye, and a potential difference measurement is a measure for the eye position.

The oxygenation of a person's hemoglobin can be monitored indirectly in a noninvasive manner using a pulse oximetry sensor, rather than measuring directly from a blood sample. The sensor is placed on a thin part of the person's body, such as a fingertip or earlobe, and a light containing both red and infrared wavelengths is passed from one side to the other. The change in absorbance of each of the two wavelengths is measured and the difference used to estimate oxygen saturation of a person's blood and changes in blood volume in the skin. A photoplethysmogram (PPG) can then be obtained using the pulse oximeter sensor or with an optical sensor using a single light source. The PPG can be used to measure blood flow and heart rate. An electroencephelogram (EEG) can be monitored using electrodes attached to the scalp and measures voltages generated by brain activity.

The converter assembly 14 converts the electrical signals generated by the sensor assembly 12 to a frequency modulated physiological audio signal that can be received by a computing device 13. In the embodiment shown in FIG. 2, the converter assembly 14 includes a converter 23 and an audio transmitter 24 for outputting frequency modulated physiological signals having a carrier frequency in the range of from about 6 kHz to about 20 kHz as frequency modulated acoustic signals. Nonlimiting examples of suitable audio transmitters 24 include, but are not limited to, miniature speakers, piezoelectric buzzers, and the like. The acoustic signals can be received by, for example, a microphone 25 in a computing device 13 such as a smartphone, personal digital assistant (PDA), tablet personal computer, pocket personal computer, notebook computer, desktop computer, server computer, and the like.

Prior art devices have used frequency modulated physiological signals to communicate between acquisition hardware and a computing device. The signals have a carrier frequency within the audible range such as the traditional 1.9 kHz FM frequency used to transmit ECG signals. However, it has been discovered that by using "high frequency" audio frequencies as the carrier, such as frequencies in the range of from about 6 kHz to about 20 kHz, the acoustic communication between the acquisition electronics 11 of the personal monitoring device 10, and a computing device 13 such as a smartphone, is virtually silent and far more noise-immune than the traditional 1.9 kHz FM ECG frequency. In fact, measurements of the audio signal power in the 1.5 kHz to 15 kHz range determined that carrier frequencies of 6 kHz and higher provide communication that is immune to ambient and voice "noise" contamination. Also, by using a carrier frequency in the 10 kHz to 15 kHz range, we create both a lower noise and a silent communication between the acquisition electronics 11 and the computing device 13 or smartphone. An additional reason for using high carrier frequencies, such as in the 6 kHz to 15 kHz range or in the 10 kHz to 15 kHz range, is to allow simultaneous recording of voice and physiological signals over a single audio channel, where voice and the FM signal are in different frequency bands that can be filtered and separated. The clinical applications of this embodiment can include fast and inexpensive cardiac rhythm diagnosis for physicians as well as personal ECG acquisition for patients.

Figure 4:
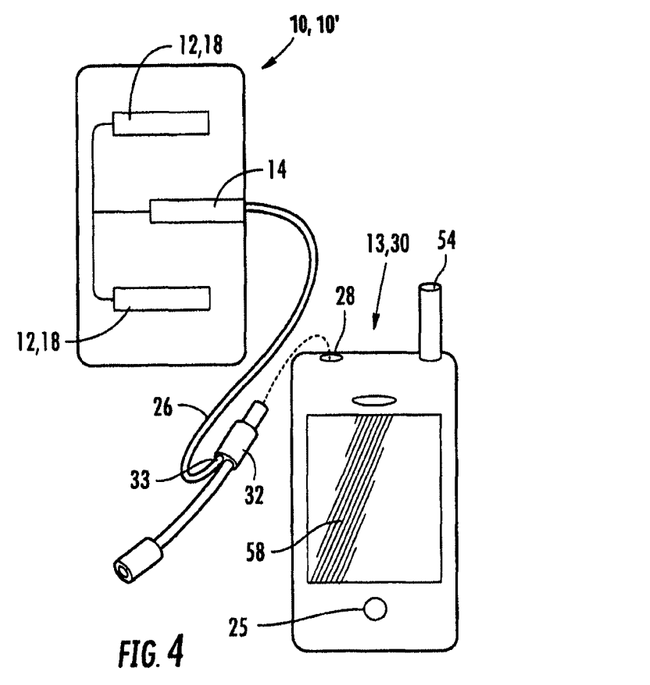
FIG. 4 is a schematic representation of an embodiment wherein a personal monitoring device includes an audio cable that can input to a smartphone.

In another embodiment, such as that shown in FIG. 4, the converter assembly 14 is configured to convert the electrical signals generated by the sensor assembly 12 to a frequency modulated physiological audio signal which is transmitted by a cable 26 to a 3.5 mm headphone jack 28 on a smartphone 30. This configuration is totally silent and immune to ambient acoustic noise. In this embodiment the converter assembly 14 is electrically isolated from the smartphone 30 by an audio isolation transformer 32. The audio isolation transformer 32 preferably conforms to medical safety performance standards such as, for example, those outlined in IEC 60601 along with national and regional deviations. The cable 26 for transmitting the frequency modulated ECG audio signal to the 3.5 mm headphone jack 28 on the smartphone 30 can include a splitter 33 configured, as understood by those skilled in the art, to allow the user to listen to music and voice messages while transmitting the frequency modulated ECG audio signal. The splitter 33 can also allow the user to utilize a mic or headset to record spoken voice messages, such as comments and notes regarding physical symptoms, simultaneously with the ECG audio signal. Using a high carrier frequency of around 10 kHz, or in the 6 kHz to 20 kHz range, allows simultaneous recording of voice and physiological signals over a single audio channel, where the voice and the frequency modulated signal are in different frequency bands that can be readily filtered and separated.

Figure 5:
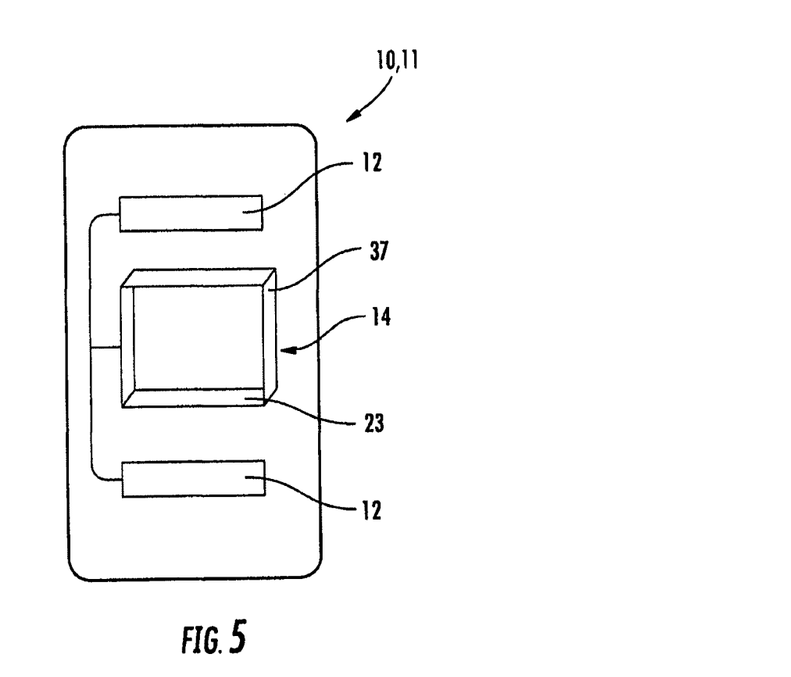
FIG. 5 is a schematic representation of an embodiment of an ECG device of the present invention utilizing a wireless radio transmitter.
Figure 6:
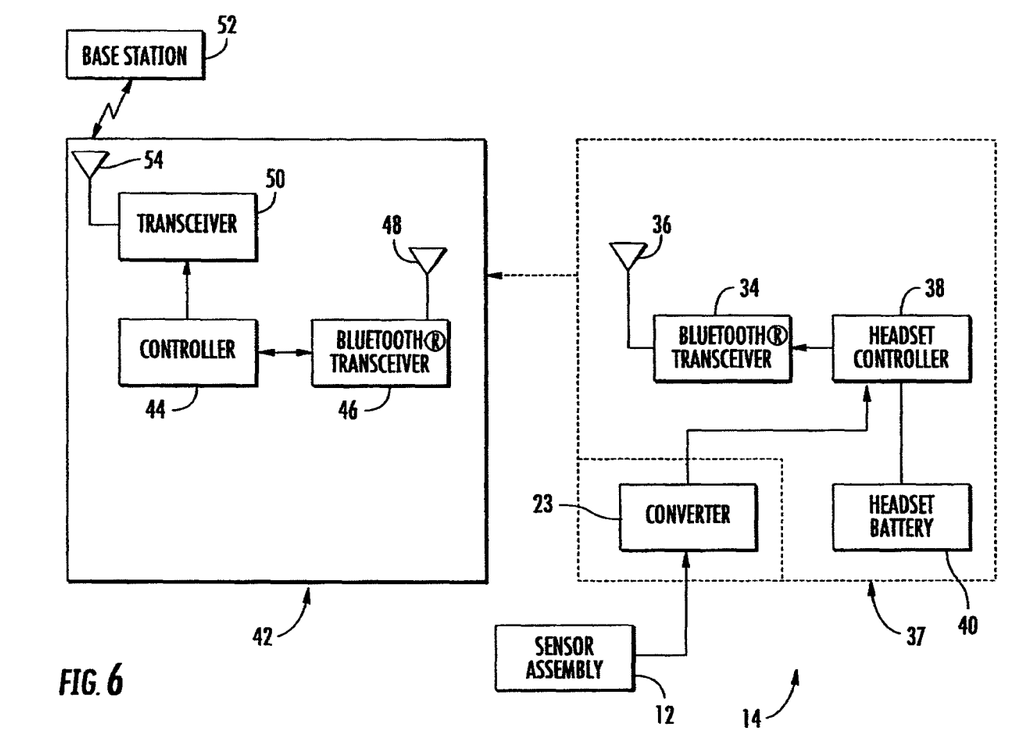
FIG. 6 is a schematic representation of an embodiment of a personal monitoring device of the present invention connecting via Bluetooth® to a computing device.

In yet another embodiment, shown in FIGS. 5 and 6, the converter assembly 14 includes a wireless radio transmitter 37 configured to convert and transmit the electrical signals generated by the sensor assembly 12 using a headset profile (HSP) of the Bluetooth® wireless communications standard is defined by the Bluetooth Special Interest Group (SIG) and available at URL address www.bluetooth.org. The electrical signals generated by the sensor assembly 12 are converted and transmitted using a Bluetooth® transceiver 34 and antenna 36 and communicated to the computing device 13, preferably a smartphone 30, according to instructions provided by a headset controller 38. Economy, as well as isolation and convenience, are provided by using a commercially available headset controller 38, Bluetooth® transceiver 34, and antenna 36, powered by a headset battery 40, wherein the electronics are commercially configured and mass-produced for communicating with computing devices 13 such as smartphones 30.

Computing device electronics 42 typically include a controller 44, a Bluetooth® transceiver 46 and antenna 48 for receiving input from a wireless Bluetooth® device. Most computing devices, and all smartphones, include a memory 56, a display screen 58, and a transceiver 50 for transmitting/receiving information signals to/from a base station or web server 52 via a cellular antenna 54. Thus, the computing device electronics 42 can be used to store information from the personal monitoring device 10 in memory 56, and/or transmit the information to the base station 52 or a specific communication address via wireless communication technology well understood by those skilled in the art.

In some cases, the personal monitoring device 10 can be considered an ECG device 10' and includes an electrode assembly 18 configured to sense heart-related signals upon contact with a user's skin, and to convert the sensed heart-related signals to an ECG electric signal. As discussed in detail hereinafter, the ECG device 10' transmits a frequency modulated ECG audio signal to a smartphone 30 via a wired audio jack connection, a wireless headset, or acoustically. Software running on the smartphone 30 digitizes and processes the audio in real-time, where the frequency modulated ECG signal is demodulated. The ECG can be further processed using algorithms to calculate heart rate and identify arrhythmias. The ECG, heart rate, and rhythm information can be displayed on the smartphone 30, stored locally for later retrieval, and/or transmitted in real-time to a web server 52 via a 2G/3G, WiFi or other Internet connection on the smartphone 30. In addition to the display and local processing of the ECG data, the smartphone 30 can transmit, in real-time, the ECG, heart rate and rhythm data via a secure web connection for viewing, storage and further analysis via a web browser interface (using the 2G/3G or WiFi connectivity of the smartphone 30). Server software provides for storage, further processing, real-time or retrospective display and formulation of a PDF ECG rhythm strip document and/or other reports and formats for printing remotely or locally.

In one embodiment, the converter assembly 14 of ECG device 10' is integrated with, and electrically connected to the electrode assembly 18 and is configured to convert the electric ECG signal generated by electrode assembly 18 to a frequency modulated ECG audio signal having a carrier frequency in the range of from about 6 kHz to about 20 kHz. It is sometimes desirable to utilize a carrier frequency in the 10 kHz to 15 kHz range in order to create both a lower noise and a silent communication between the acquisition electronics 11 and the computing device 13 or smartphone 30.

Figure 7:
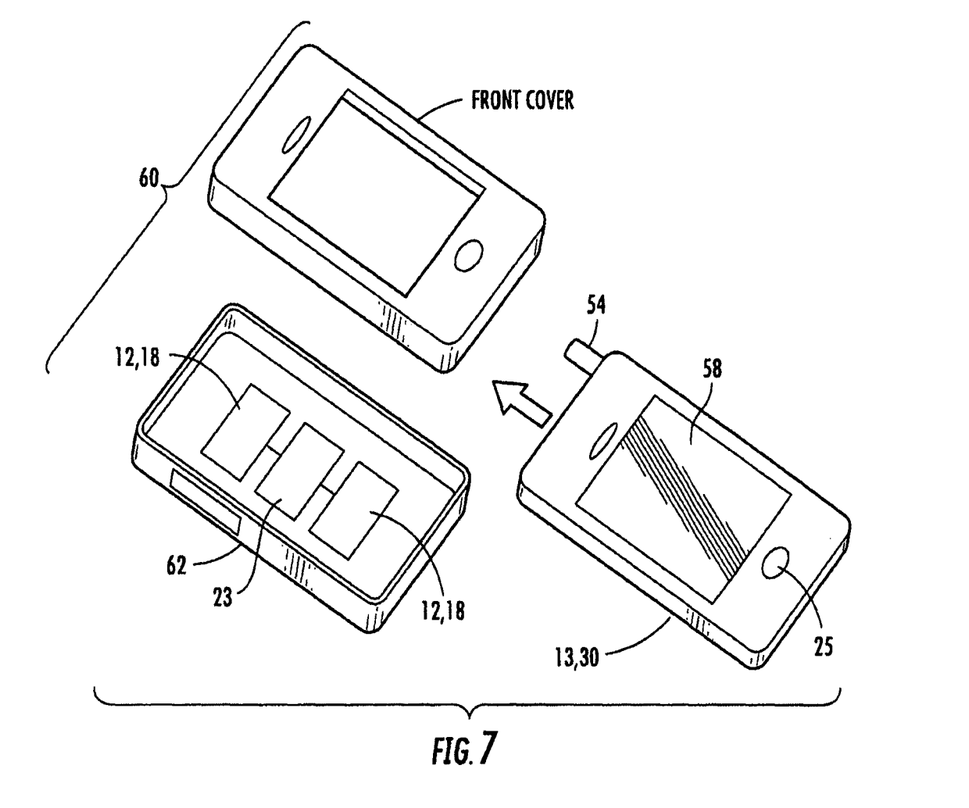
FIG. 7 is a schematic representation of an embodiment of a personal monitoring device of the present invention.

In one configuration, the ECG device 10' is usable as a smartphone protective case 60 as shown in FIG. 7. One example configuration utilizes a "slip-on" protective case 60 for an iPhone® or other smartphone 30, the protective case 60 including an integrated ECG electrode assembly 18 and acquisition electronics 11 (2, 3 or 4 electrodes for generating a single lead of ECG data). The ECG electrodes are located on the side 62 of the case 60 opposite of the display screen 58. The smartphone 30, in its ECG-adapted protective case 60, is held in both hands (generating a lead one, Left Arm minus Right Arm) or is placed on a person's chest to generate a modified chest lead. The ECG is measured by the acquisition electronics 11 and converted into a frequency modulated signal with a carrier or center frequency from about 6 kHz to 20 kHz, or in some embodiments from 10 kHz to 15 kHz. The frequency modulated signal is output by a miniature speaker 64 or a piezoelectric buzzer 66.

In another configuration, the ECG device 10', as shown schematically in FIG. 2, is usable as a standalone real-time ECG acquisition device. The ECG device is identical to the "case" electronics, but is present in its own housing 67 rather than being integrated into a protective case 60 for a smartphone 30. This embodiment allows for use of the device to acquire ECG data and have it communicated acoustically to a PC or other computing device for demodulation, processing, storage and display via a web application and connection.

In either configuration, the smartphone 30 utilizes its built-in microphone 25 and CPU to acquire, digitize, demodulate, process and then display the ECG data in real-time. Also, the smartphone 30 can calculate a real-time heart rate measurement and determine a cardiac rhythm diagnosis like atrial fibrillation. The smartphone 30 can utilize its 2G, 3G, Bluetooth® and WiFi connectivity to transmit the ECG and other data to a secure web server 52 for real-time distant display, storage and analysis. Also, the ECG data can be stored locally on the smartphone 30 for later review or transmission.

Figure 8:
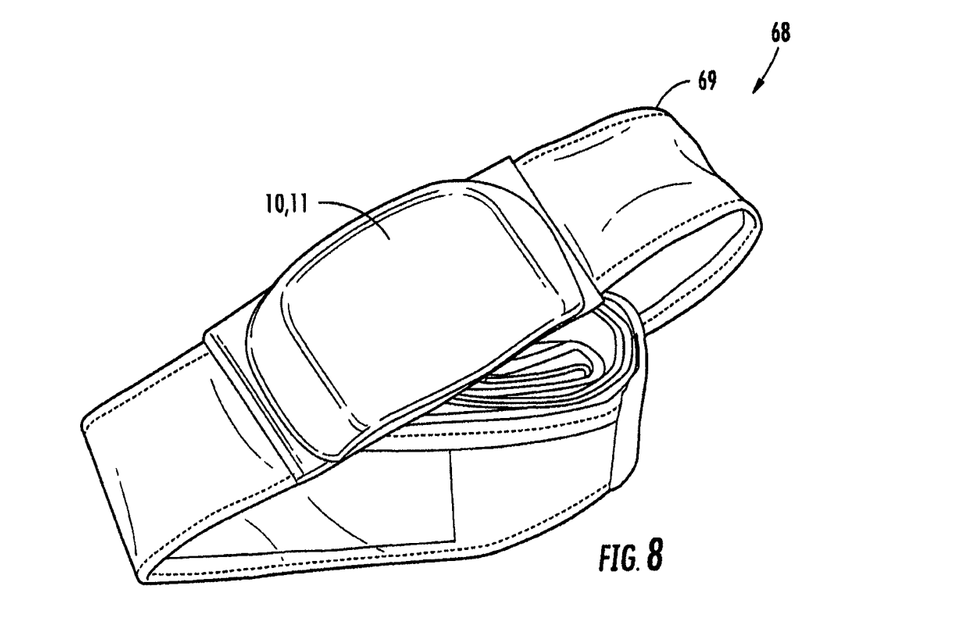
FIG. 8 is a schematic representation of an embodiment of an ECG device of the present invention included positioned within a chest strap.

In another embodiment, shown schematically in FIG. 8, the ECG device 10' is usable as a chest strap device 68 like a fitness heart rate monitor. The chest strap 69 with integrated ECG electrode assembly 18 and acquisition electronics 11 "pod" generate the frequency modulated ECG signal and send it by one of two modes to the smartphone 30. In one mode, a cable 26, as described above, plugs into the 3.5 mm headphone jack 28 on the iPhone®, Blackberry® or other smartphone 30 which provides an audio input (normally used for a headphone mic). This configuration is totally silent and immune to ambient acoustic noise. The ECG data is isolated from the smartphone 30 by an audio isolation transformer 32. In another mode, the frequency modulated audio signal is transmitted by a Bluetooth® headset chip, as described above, and the smartphone 30 receives it and performs the other processing steps. This configuration preferably makes use of mass-produced headset electronics and includes a rechargeable battery. This configuration is wireless, which provides isolation and convenience.

Software on the smartphone 30 can also combine data and signals from other sensors built into the smartphone 30 such as a GPS and accelerometer. Further processing of this data provides additional information related to the user, such as speed, location, distance, steps, cadence, body position, fall detection and energy expenditure. The raw signals from the sensors and derived information can be displayed and stored locally on the smartphone 30, as well as being transmitted to the web server 52 over an Internet connection. Software on the web server 52 provides a web browser interface for real-time or retrospective display of the signals and information received from the smartphone 30, and also includes further analysis and reporting.

Figure 9:
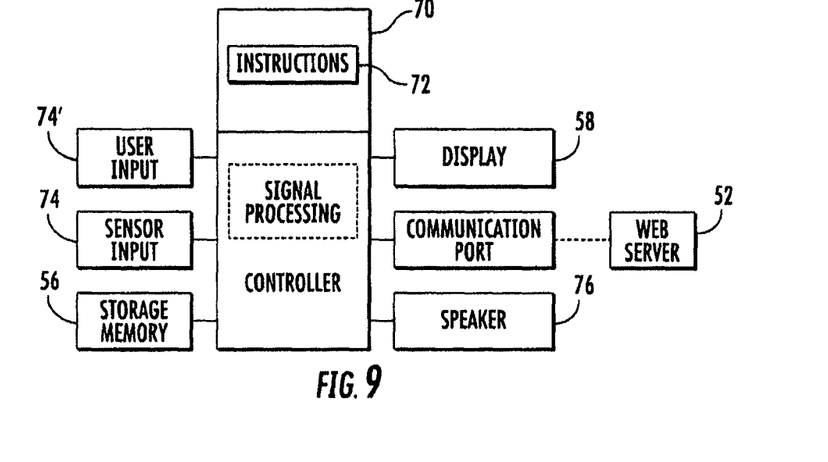
FIG. 9 is a schematic representation of a computer-readable storage medium embodiment of the present invention.

Referring now to FIG. 9, a computer-readable storage medium 56 stores a set of instructions 72, wherein the instructions 72 are capable of being executed by one or more computing devices 13. Nonlimiting examples of suitable computing devices 13 include smartphones 30, personal digital assistants (PDAs), tablet personal computers, pocket personal computers, notebook computers, desktop computers, and server computers. When executed, the one or more computing devices 13 is caused to digitize and demodulate a sensor input 74 such as a frequency modulated ECG audio signal having a carrier frequency in the range of from about 6 kHz to about 20 kHz to produce real-time demodulated digital ECG data. The instructions 72 can cause the real-time demodulated digital ECG data to display on a display screen 58 of the computing device 13.

Sensor input 74 can also include real-time information from additional sensors as well as user input 74'. For example, in embodiments wherein the computing device 13 is a smartphone 30, the input 74 can include real-time information from a GPS and/or accelerometer in the smartphone 30 in addition to the demodulated digital ECG data. User input 74' can also include spoken voice messages entered through a microphone of the computing device 13. Instructions 72 can cause the sensor and/or user input 74 and 74' to be recorded and maintained in a storage memory 56 of the computing device 13.

In one embodiment, the set of instructions 72, when executed by the one or more computing devices 13, can further cause the one or more computing devices 13 to calculate and display in real-time, a heart rate represented by the frequency modulated ECG audio signal. In addition, demodulated digital ECG data can be processed to identify the occurrence of an arrhythmia. In such designs, the storage medium 70 can include instructions 72 to cause the computing device 13 to display a warning on a display screen 58 or emit an audible alert through the speaker 76 at the occurrence of an arrhythmia.

Instructions 72 can cause the computing device 13 to store the demodulated digital ECG data in a memory 56 of the one or more computing devices 13 for later retrieval. The set of instructions 72 can further cause the one or more computing devices 13 to retrieve and transmit, upon demand, the stored demodulated digital ECG data to a web server 52 via an internet connection on the computing device 13. Recorded spoken voice messages can be stored and transmitted to the web server 52, simultaneously with the demodulated digital ECG data.

In other embodiments, the instructions 72 can cause the one or more computing devices 13 to transmit the demodulated digital ECG data, and/or voice messages, to the web server 52 in real-time.

A version of the smartphone software is packaged as a software library that can be integrated with other third party software applications. This provides a simplified and standard method for third party applications to use the ECG device 10' to obtain heart rate and other derived information without having to develop their own data acquisition, demodulation, and signal processing algorithms.

A version of the software also runs on a PC and includes demodulation, processing, storage and transmission to the web server 52. The software includes the audio acquisition, demodulation, ECG analysis, and acceleration analysis modules.

The audio acquisition module selects the appropriate audio input and samples the audio. On the iPhone®, audio is sampled and processed using the audio unit framework, which provides low latency audio acquisition and processing. The audio unit framework also allows automatic selection of the appropriate audio source, internal mic, audio jack connection, or Bluetooth® headset. The sampling rate will typically be at 44 kHz when the modulation carrier frequency is greater than 10 kHz, but for lower carrier frequencies, it may use a lower audio sampling rate. On other devices this module will use the most appropriate API's for efficient, low latency audio sampling.

The demodulation module demodulates a frequency modulated ECG audio signal, using a linear approximation and zero crossings algorithm. The demodulator allows selection of different modulation parameters to match the particular ECG device. Demodulation using zero crossings and linear approximation works well for carrier frequencies 6 kHz and lower and has the advantage that it is simple and fast. Above 10 kHz with 44 kHz sampling, the errors from linear approximation become large, although the effect is somewhat reduced if applying a 40 Hz filter to the demodulated ECG. Application of sine or other curve fitting methods can be used to reduce the error associated with linear approximation for carrier frequencies above 10 kHz. Audio samples from the audio acquisition module are first passed through a digital band-pass filter to remove unwanted frequencies outside the modulation range. The digital band-pass filter is most effective when receiving acoustically coupled audio which can be contaminated with noise. When using a center frequency above 6 kHz, the band-pass filter is able to provide good noise immunity from voice and background ambient noise which is typically below 5 kHz. The band-pass filter stage could be eliminated to save processing power when receiving audio via a wired or Bluetooth® connection which would not be susceptible to background noise contamination. To demodulate the signal it is necessary to estimate the frequency of the audio waveform. The algorithm looks at the sign of incoming data. When the sign changes it draws a straight line between the two points and interpolates the zero value. It uses this to determine the average frequency over a 3.333 ms interval, which provides ECG data at the output sampling rate of 300 Hz.

The ECG analysis module includes algorithms that process the ECG to detect and classify beats, and provides a heart rate estimate. Beat-to-beat heart rate is calculated from the interval between beats and a more robust measurement of heart rate is calculated using median filtering of the RR intervals.

The acceleration analysis module includes algorithms that process signals from the built-in 3 axis accelerometer sensor in the smartphone 30, to derive an estimate of a person's energy expenditure, steps, cadence, and body position and to detect falls.

From the above descriptions, it is clear that the presently disclosed and claimed inventive concept(s) are well-adapted to carry out the objects and to attain the advantages mentioned herein, as well as those inherent in the presently disclosed and claimed inventive concept(s). While the presented embodiments have been described for purposes of this disclosure, it will be understood that numerous changes may be made which will readily suggest themselves to those skilled in the art and which are accomplished within the spirit of the presently disclosed and claimed inventive concept(s).

What is claimed is:

1. A mobile ECG device comprising:
    an electrode assembly comprising at least 3 electrodes, wherein the electrodes are to concurrently sense heart-related signals upon contact with a user's skin, and to produce electrical signals representing the sensed heart-related signals;
    a converter assembly electrically connected to the electrode assembly, configured to convert the electrical signals to a modulated physiological audio signal, wherein the modulated physiological audio signal carries information representing the sensed heart-related signals; and
    a wireless acoustic transmitter that directly transmits the modulated physiological audio signal wirelessly to a computing device.

2. The mobile ECG device according to claim 1, wherein the modulated physiological audio signal is a frequency modulated physiological audio signal, wherein the wireless acoustic transmitter outputs the frequency modulated physiological audio signal having a carrier frequency in the range of from about 6 kHz to about 20 kHz.

3. The mobile ECG device according to claim 1, wherein the modulated physiological audio signal is in accordance with Bluetooth® protocol.

4. The mobile ECG device according to claim 3, wherein the modulated physiological audio signal is in accordance with a headset profile of the Bluetooth® protocol.

5. The mobile ECG device according to claim 3, wherein the electrode assembly comprises 4 electrodes.

6. The mobile ECG device according to claim 5, wherein the electrode assembly comprises 3 electrodes, and wherein at least 2 of the 3 electrodes connect to the electrode assembly by wires.

7. The mobile ECG device in accordance with claim 1 further comprising:
    a chest strap, wherein the electrode assembly is positioned within the chest strap and wherein the electrode assembly comprises:
    at least two electrically isolated electrodes secured on the chest strap such that when the strap is secured to the user the at least two electrically isolated electrodes contact the user's skin on a left side and a right side of the user's chest to form Lead I.

8. The mobile ECG device according to claim 7, wherein the modulated physiological audio signal is in accordance with Bluetooth® protocol.

9. The mobile ECG device according to claim 8, wherein the modulated physiological audio signal is in accordance with a headset profile of the Bluetooth® protocol.

10. The mobile ECG device according to claim 1, wherein the modulated physiological audio signal is accordance with WiFi protocol.

* * * * *